(12) United States Patent
Fu

(10) Patent No.: US 12,290,474 B2
(45) Date of Patent: May 6, 2025

(54) OPHTHALMIC LASER SURGICAL SYSTEM AND METHOD FOR WAVEFRONT-GUIDED CORNEAL LENTICULE EXTRACTION FOR VISION CORRECTION

(71) Applicant: AMO Development, LLC, Irvine, CA (US)

(72) Inventor: Hong Fu, Pleasanton, CA (US)

(73) Assignee: AMO Development, LLC, Irvine, CA (US)

(*) Notice: Subject to any disclaimer, the term of this patent is extended or adjusted under 35 U.S.C. 154(b) by 497 days.

(21) Appl. No.: 17/653,127

(22) Filed: Mar. 1, 2022

(65) Prior Publication Data
US 2023/0277377 A1    Sep. 7, 2023

(51) Int. Cl.
*A61F 9/008* (2006.01)
*A61F 9/013* (2006.01)

(52) U.S. Cl.
CPC .......... *A61F 9/00827* (2013.01); *A61F 9/013* (2013.01); *A61F 2009/0088* (2013.01)

(58) Field of Classification Search
CPC .. A61F 9/00827; A61F 9/00829; A61F 9/013; A61F 2009/00848; A61F 2009/00872; A61F 2009/0088
See application file for complete search history.

(56) References Cited

U.S. PATENT DOCUMENTS

| 2010/0114076 | A1 | 5/2010 | Reinstein et al. |
| 2016/0089270 | A1 | 3/2016 | Fu |
| 2018/0008461 | A1* | 1/2018 | Fu ..................... A61F 9/00829 |
| 2020/0046558 | A1 | 2/2020 | Fu et al. |

FOREIGN PATENT DOCUMENTS

| WO | 2011087831 A1 | 7/2011 |
| WO | 2017025115 A1 | 2/2017 |

* cited by examiner

*Primary Examiner* — Rex R Holmes
*Assistant Examiner* — Shreya Anjaria

(57) ABSTRACT

A ophthalmic laser-assisted corneal lenticule extraction procedure that uses wavefront measurements to guide the formation of the corneal lenticule. The wavefront map measured from a free eye using a wavefront aberrometer is registered to the cornea of a docked eye based on comparisons of iris images and corneal markings. The docked-eye cornea-registered wavefront map is then corrected to be consistent with the Munnerlyn formula for the spherical power, and adjusted for any physician adjustments and/or myopia error due to a flat add in the lenticule, using Zernike polynomials. The corrected and adjusted wavefront map is then used to calculate the profiles of the bottom and top lenticule incisions in the applanated cornea, where higher-order components in the wavefront map are distributed to the bottom lenticule incision alone and lower-order components in the wavefront map are distributed to both the bottom and the top lenticule incision.

11 Claims, 10 Drawing Sheets

| nc | 1.3770 | Ratio=Munnerlyn/ThinPhasePlate | | | Thin Phase Plate (μm/D) | | | Munnerlyn Model (μm/D) | | |
|---|---|---|---|---|---|---|---|---|---|---|
| nk | 1.3375 | Optical Zone (mm) | | | Optical Zone (mm) | | | Optical Zone (mm) | | |
| K1=K2 (D) | RoC (mm) | 5.5 | 6.0 | 6.5 | 5.5 | 6.0 | 6.5 | 5.5 | 6.0 | 6.5 |
| 33.0 | 10.23 | 104.7% | 105.6% | 106.7% | 10.0 | 11.9 | 14.0 | 10.5 | 12.6 | 14.9 |
| 35.0 | 9.64 | 105.3% | 106.4% | 107.6% | 10.0 | 11.9 | 14.0 | 10.6 | 12.7 | 15.1 |
| 38.0 | 8.88 | 106.3% | 107.6% | 109.1% | 10.0 | 11.9 | 14.0 | 10.7 | 12.8 | 15.3 |
| 40.0 | 8.44 | 107.1% | 108.5% | 110.2% | 10.0 | 11.9 | 14.0 | 10.7 | 13.0 | 15.4 |
| 43.5 | 7.76 | 108.5% | 110.3% | 112.3% | 10.0 | 11.9 | 14.0 | 10.9 | 13.1628 | 15.7 |
| 45.0 | 7.50 | 109.1% | 111.1% | 113.3% | 10.0 | 11.9 | 14.0 | 10.9 | 13.3 | 15.9 |
| 47.0 | 7.18 | 110.1% | 112.2% | 114.7% | 10.0 | 11.9 | 14.0 | 11.0 | 13.4 | 16.1 |
| 50.0 | 6.75 | 111.6% | 114.1% | 117.1% | 10.0 | 11.9 | 14.0 | 11.2 | 13.6 | 16.4 |
| 53.0 | 6.37 | 113.2% | 116.2% | 119.7% | 10.0 | 11.9 | 14.0 | 11.4 | 13.9 | 16.8 |
| 56.0 | 6.03 | 115.0% | 118.5% | 122.6% | 10.0 | 11.9 | 14.0 | 11.5 | 14.1 | 17.2 |

OPHTHALMIC LASER SURGICAL SYSTEM AND METHOD FOR WAVEFRONT-GUIDED CORNEAL LENTICULE EXTRACTION FOR VISION CORRECTION

BACKGROUND OF THE INVENTION

Field of the Invention

This invention relates to ophthalmic laser surgical systems and methods, and in particular, it relates to a wavefront-guided corneal lenticule extraction procedure for vision correction.

Description of Related Art

Vision impairments such as myopia (near-sightedness), hyperopia (far-sightedness) and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm.

Prior surgical approaches for reshaping the cornea include laser assisted in situ keratomileusis (LASIK), photorefractive keratectomy (PRK) and corneal lenticule extraction.

In the LASIK procedure, an ultra-short pulsed laser is used to cut a corneal flap to expose the corneal stroma for photoablation with ultraviolet beams from an excimer laser. Photoablation of the corneal stroma reshapes the cornea and corrects the refractive condition such as myopia, hyperopia, astigmatism, and the like. In a PRK procedure where no flap is created, the epithelium layer is first removed, and some stroma material is then removed by an excimer laser. The epithelium layer will grow back within a few days after the procedure.

In a corneal lenticule extraction procedure, instead of ablating corneal tissue with an excimer laser following the creation of a corneal flap, the technique involves tissue removal with two or more femtosecond laser incisions that intersect to create a lenticule for extraction. The extraction of the lenticule changes the shape of the cornea and its optical power to accomplish vision correction. Lenticular extractions can be performed either with or without the creation of a corneal flap. With the flapless procedure, a refractive lenticule is created in the intact portion of the anterior cornea and removed through a small incision. Methods for corneal lenticule extraction using a fast-scan-slow-sweep scheme of a surgical ophthalmic laser system are described in U.S. Pat. Appl. Pub. No. 20160089270, entitled "Systems And Methods For Lenticular Laser Incision," published Mar. 31, 2016, and U.S. Pat. Appl. Pub. No. 20200046558, entitled "High Speed Corneal Lenticular Incision Using A Femtosecond Laser," published Feb. 13, 2020.

SUMMARY

The present invention is directed to an ophthalmic laser surgical system and method for wavefront-guided corneal lenticule extraction that substantially obviates one or more of the problems due to limitations and disadvantages of the related art.

An object of the present invention is to perform corneal lenticule extraction with higher accuracy and achieve higher order aberration correction.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a method implemented in an ophthalmic laser system for forming lenticule incisions in a cornea of an eye, which includes: coupling the eye to the ophthalmic laser system to applanate the eye; obtaining a wavefront map which has been registered to the cornea of the applanated eye and defined at an anterior surface of the cornea; calculating a lenticule thickness profile which represents a thickness of cornea tissue to be removed based on the wavefront map and a correction factor using $$\Delta(r, \varphi) = \frac{2R_K^2}{\left[\frac{n_c-1}{n_c} \cdot L^2 + \sqrt{R_K^2 - L^2} \cdot \left(R_K + \sqrt{R_K^2 - L^2}\right)\right]} \cdot \frac{W_{max} - W(r, \varphi)}{n_c - 1} \equiv$$

$$\gamma_{MT} \cdot \frac{W_{max} - W(r, \varphi)}{n_c - 1}$$

where $\Delta(r, \varphi)$ is the lenticule thickness as a function of a radius r from a Z axis and a meridian angle $\varphi$ around the Z axis, $R_K$ is an average radius of curvature of the cornea anterior surface before applanation, L is a radius of an optical zone of the lenticule, $n_c$ is a refractive index of the cornea, $W(r, \varphi)$ is the wavefront map, $W_{max}$ is a parameter corresponding to a maximum value of the wavefront, and $\gamma_{MT}$ denotes the correction factor; calculating cutting profiles for a bottom lenticule incision surface and a top lenticule incision surface based on the lenticule thickness profile; and operating the ophthalmic laser system to incise the cornea according to the cutting profiles to form the bottom and top lenticule incision surfaces.

In another aspect, the present invention provides a method implemented in an ophthalmic laser system for incising a lenticule in a cornea of an eye, which includes: coupling the eye to the ophthalmic laser system to applanate the eye; obtaining a wavefront map which has been registered to the cornea of the applanated eye and defined at an anterior surface of the cornea; expressing the wavefront map as a sum of a plurality of Zernike polynomials including a plurality of lower-order Zernike polynomials and a plurality of higher-order Zernike polynomials; dividing the wavefront map into a lower-order part containing only the lower-order Zernike polynomials and a higher-order part containing only the higher-order Zernike polynomials; calculating a bottom lenticule incision profile containing all of the higher-order part and a portion of the lower-order part of the wavefront map; calculating a top lenticule incision profile containing only a remaining portion the lower-order part of the wavefront map and no portion of the higher-order part of the wavefront map; and operating the ophthalmic laser system to incise the cornea according to the bottom and top lenticule incision profiles to form the bottom and top lenticule incision surfaces. In preferred embodiments, the lower-order Zernike polynomials include a third, a fourth and a fifth Zernike polynomials and the higher-order Zernike polynomials a sixth and higher Zernike polynomials.

In some embodiments, the step of obtaining the wavefront map includes: before coupling the eye to the ophthalmic laser system: using a wavefront aberrometer, measuring an original wavefront map, and taking a first image of the eye including an iris of the eye; forming a plurality of marks on the cornea; using a camera of the ophthalmic laser system, taking a second image of the eye including the corneal marks overlaying the iris; and based on the first and second images of the eye, registering the original wavefront map to the corneal marks in the second image to obtain a free-eye cornea-registered wavefront map; and after coupling the eye to the ophthalmic laser system: using a camera of the ophthalmic laser system, taking a third image of the eye including the corneal marks that have been deformed by the coupling of the eye to the ophthalmic laser system; and based on the second and third images of the eye, registering the free-eye cornea-registered wavefront map to the corneal marks in the third image to obtain the wavefront map.

In some embodiments, the step of obtaining the wavefront map includes: obtaining an input wavefront map which has been registered to the cornea of the applanated eye and defined at an anterior surface of the cornea; expressing the input wavefront map as a sum of a plurality of Zernike polynomials to obtain a plurality of original Zernike coefficients; calculating spherical and cylindrical powers at cornea plane for optical infinity based on some of the original Zernike coefficients; converting the spherical and cylindrical powers at cornea plane for optical infinity to equivalent values of spherical and cylindrical powers under defined manifest measurement conditions; receiving adjustments of spherical and cylindrical powers as input; adding the adjustments of spherical and cylindrical powers to the equivalent values of spherical and cylindrical powers to obtain adjusted spherical and cylindrical powers under the defined manifest measurement conditions; converting the adjusted spherical and cylindrical powers to equivalent values of adjusted spherical and cylindrical powers at cornea plane for optical infinity; calculating adjusted Zernike coefficients based on the original Zernike coefficients and the adjusted spherical and cylindrical powers at cornea plane for optical infinity; and calculating an adjusted wavefront map as a sum of the plurality of Zernike polynomials using the adjusted Zernike coefficients.

In some embodiments, the lenticule thickness profile includes a flat-add layer of uniform thickness, and wherein the step of obtaining the wavefront map includes: obtaining an input wavefront map which has been registered to the cornea of the applanated eye and defined at an anterior surface of the cornea; expressing the input wavefront map as a sum of a plurality of Zernike polynomials to obtain a plurality of original Zernike coefficients; calculating a spherical power at cornea plane for optical infinity based on some of the original Zernike coefficients; adding a flat-add correction to the spherical power at cornea plane for optical infinity, wherein the flat-add correction is a spherical power correction calculated based on the uniform thickness of the flat-add layer; calculating adjusted Zernike coefficients based on the original Zernike coefficients and the adjusted spherical power at cornea plane for optical infinity; and calculating an adjusted wavefront map as a sum of the plurality of Zernike polynomial using the adjusted Zernike coefficients.

In another aspect, the present invention provides an ophthalmic surgical laser system which includes: a laser source configured to generate a pulsed laser beam comprising a plurality of laser pulses; a laser delivery system configured to deliver the pulsed laser beam to a cornea of an eye coupled to the laser delivery system; an XY-scanner configured to scan the pulsed laser beam in the cornea; a Z-scanner configured to modify a depth of a focus of the pulsed laser beam; and a controller configured to control the laser source, the XY-scanner and the Z-scanner to form lenticule incisions in the cornea, including some or all of the method steps describe above.

It is to be understood that both the foregoing general description and the following detailed description are exemplary and explanatory and are intended to provide further explanation of the invention as claimed.

DETAILED DESCRIPTION OF PREFERRED EMBODIMENTS

Embodiments of the present invention relate to a corneal lenticule extraction method that uses wavefront measurements to guide the planning and execution of lenticular incisions. The method can more accurately form the lenticule in the cornea to be extracted for vision correction.

Figure 1:
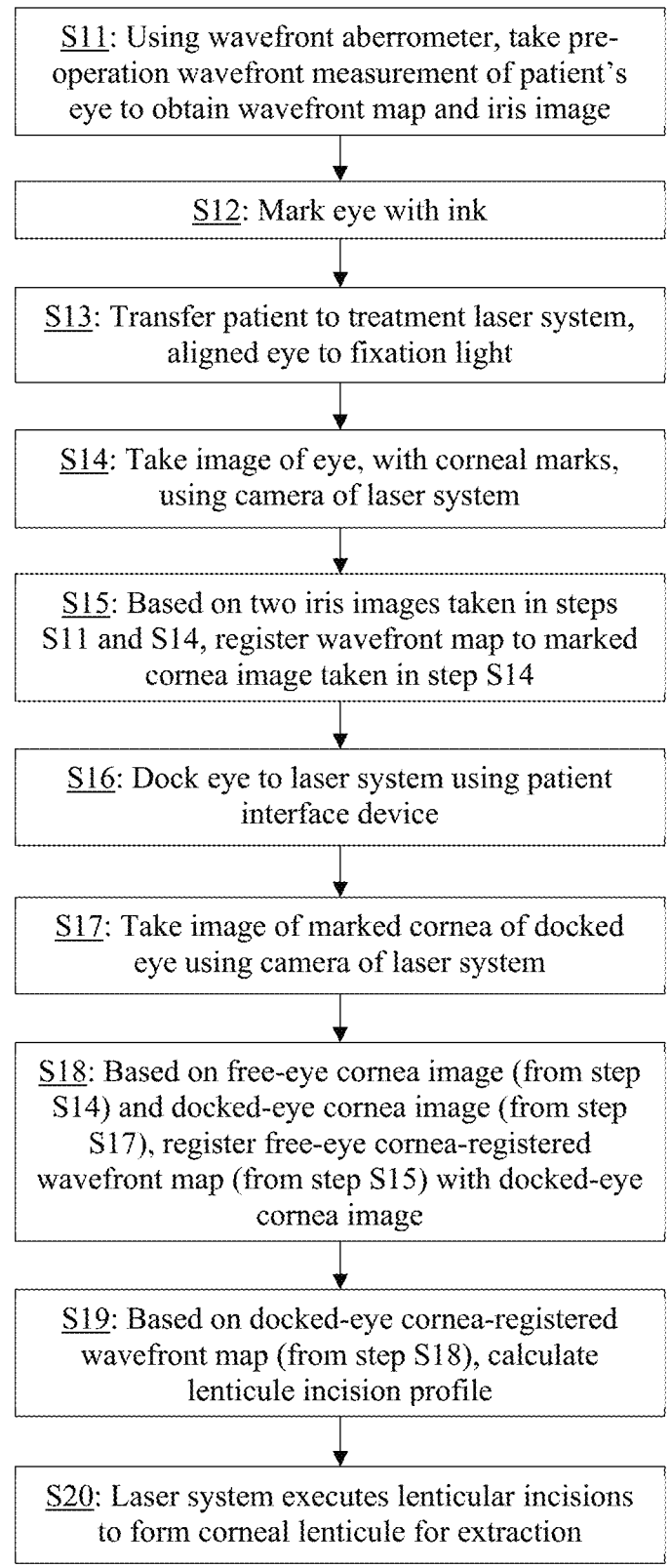
FIG. 1 is a flow diagram illustrating a method of wavefront-guided corneal lenticule extraction procedure using a wavefront aberrometer and an ophthalmic laser system according to embodiments of the present invention.

FIG. 1 schematically illustrates the overall process of a wavefront-guided corneal lenticule extraction procedure according to embodiments of the present invention. First, a pre-operation wavefront measurement is taken of a patient's eye to obtain a wavefront map and an iris image of the eye to be treated (step S11). The wavefront may be measured using a wavefront aberrometer which employs a wavefront sensor, such as a Hartmann-Shack sensor. The iris image is taken by a coaxially aligned iris registration camera simultaneously with wavefront map measurement. The iris image provides XY coordinates for the wavefront map; i.e., the wavefront map is registered (e.g., aligned) on the iris image.

This measurement is taken with the eye in its free (un-applanated) condition. Then, the eye is marked (step S12), for example, by applying surgical ink marks to the cornea surface, with the eye in the un-applanated condition. The marks form a pattern designed such that it provides sufficient coordinate information for cornea displacement when the eye is later under applanation. The mark should cover different locations of the cornea, and its shape should also be easily recognizable from the image. For example, the mark pattern may include various combinations of concentric circles or arcs, radial lines, etc.

The patient is then transferred to the treatment laser system, and the eye is aligned to a fixation light of the laser system (step S13). The eye is still in its free condition. An image is taken of the eye, with the corneal marks, using a camera of the laser system (step S14). This image includes the corneal marks overlaying the iris image. Note that if the depth of focus of the camera is too short to clearly image both the corneal marks and the iris in one image, two respective images may be taken within a short time period (such as within 0.5 second), for example by using an autofocusing camera, and combined.

Based on the two iris images taken in step S11 and step S14, the wavefront map is registered to the marked cornea image taken in step S14 (step S15). This may be accomplished by calculating a coordinates transformation that transforms the first iris image taken in step S11 to the second iris image taken in step S14, then applying the calculated coordinate transformation to the wavefront map. This registration step is performed because the wavefront aberrometer and the treatment laser system are separate apparatuses and use separate cameras, and the two iris images may be shifted, rotated, scaled, and/or otherwise distorted relative to each other. This registration step aligns the wavefront map measured with the aberrometer to the iris image taken by the camera of the laser system.

After taking the image in step S14, the eye is docked to the laser system using a patient interface device (step S16). This includes coupling the patient interface device to both the eye and the laser system. In some embodiments, the patient interface device includes a contact lens that contacts the cornea surface of the eye, which results in applanation (flattening) of the cornea. The contact lens surface may be flat or curved, resulting in different degrees of applanation. In other embodiments, the patient interface device uses a liquid filled between the cornea surface and a patient interface lens. In this case, cornea deformation may be caused by a suction ring of the patient interface which contacts the eye's surface and applies a suction force to the eye surface. Various patient interface devices are known in the art.

Another image of the marked cornea is taken using the camera of the laser system while the eye is in the docked and applanated state (step S17). Due to deformation of the docked eye, the shape of the corneal marks in this image (docked-eye cornea image) will be different from that in the free-eye cornea image taken in step S14. For example, a round circle in the original corneal mark may become an oval and its center may be shifted.

Based on the free-eye cornea image taken in step S14 and the docked-eye cornea image taken in step S17, the free-eye cornea-registered wavefront map obtained in step S15 is registered with the docked-eye cornea image (step S18). This may be accomplished by calculating a coordinate transformation that transforms the corneal marks in the free-eye cornea image to the corneal marks in the docked-eye cornea image, then applying the calculated coordinate transformation to the wavefront map to transform the free-eye cornea-registered wavefront map to a docked-eye cornea-registered wavefront map.

Thereafter, the corneal lenticule profile in the docked eye is calculated based on the docked-eye cornea-registered wavefront map (step S19). This includes calculating the shape of the top lenticular incision and the bottom lenticular incision. The laser system then executes the lenticular incisions to form a corneal lenticule (step S20), which is subsequently extracted from the cornea.

The step S19 of calculating the lenticule profile based on the docked-eye cornea-registered wavefront map is described in more detail below. In the descriptions below, the docked-eye cornea-registered wavefront map is simply referred to as the wavefront map for convenience.

As a preliminary step, if the wavefront aberrometer employed in step S11 measures the wavefront at the pupil plane, the wavefront map is propagated from the pupil plane to the corneal plane (the cornea anterior surface). This may be done by ray tracing, assuming that the rays emitting from the fovea are parallel to the wavefront aberrometer's optical axis after exiting the cornea (the position error due to this approximation is negligible).

Thin Phase Plate Model and Munnerlyn Correction

Figure 2:
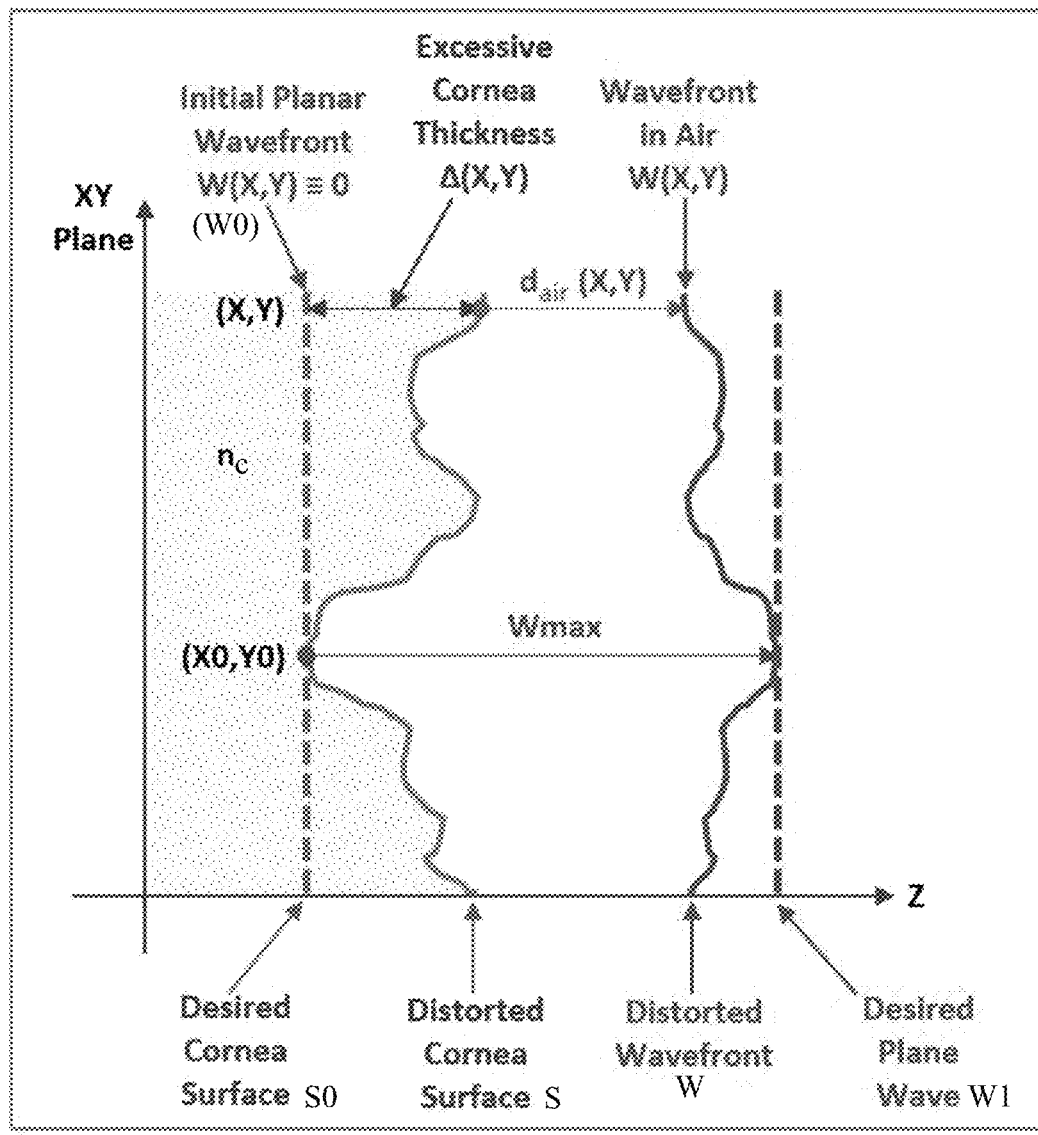
FIG. 2 schematically illustrates a thin phase plate model showing the relationship between wavefront error and the corresponding amount of cornea tissue removal for wavefront error correction.

To calculate the lenticule shape based on the wavefront map, a thin phase plate model is used. The thin phase plate model describes the relationship between the wavefront error and the amount of cornea tissue removal that corrects the wavefront error, as schematically illustrated in FIG. 2. Note that the various curves in FIG. 2 are exaggerated for convenience of illustration. In FIG. 2, the XY plane is a plane transverse to a depth direction Z of the eye.

FIG. 2 illustrates the measured wavefront in air $W(x,y)$, a desired planar wavefront $W1$, as well as the initial planar wavefront $W0$ ($W(x,y)=0$) that is transmitted from inside the cornea through the cornea surface to generate the measured wavefront. FIG. 2 also illustrates the cornea surface $S(x,y)$ prior to treatment, and the desired cornea surface $S0$ after treatment. The area shown in FIG. 2 to the left of the surface $S(x,y)$ is the cornea, having a refractive index $n_c$ (which is conventionally set at $n_c=1.3770$). The wavefront $W(x,y)$ is a distorted wavefront generated by the distorted shape of the cornea surface $S$, while the desired cornea surface $S0$ will generate the desired planar wavefront $W1$. The difference $\Delta(x,y)$ between the distorted cornea surface $S(x,y)$ and the desired cornea surface $S0$ is the excessive cornea thickness to be removed by the lenticule extraction procedure.

Note that the desired cornea surface $S0$ is placed at the minimum point $(x0,y0)$ of the distorted cornea surface, which gives the minimum amount of excessive cornea thickness $\Delta(x,y)$. The initial wavefront $W0$ is defined at the same location, and the desired planar wavefront W1 is defined at the corresponding maximum point of the distorted wavefront W(x,y). The distance between the desired planar wavefront W1 and the initial wavefront W0 at this location (x0,y0) is denoted $W_{max}$. At a given (x,y) location, the distance $d_{air}(x,y)$ between the cornea surface S(x,y) and the wavefront W(x,y) is the distance traveled by the wave in the air at that location. According to the thin phase plate model, $$\Delta(x,y) + d_{air}(x,y) = W(x,y)$$

$$n_c \cdot \Delta(x,y) + d_{air}(x,y) = W_{max}$$

which gives the cornea thickness to be removed (Eq. (1)):

$$\Delta(x, y) = \frac{W_{max} - W(r, \varphi)}{n_c - 1}$$

The thin phase plate model assumes that all rays propagate in parallel and are normal to the cornea tissue and the wavefront sensor. However, because the cornea surface of a free eye is convex and the lenticule is a positive meniscus shape, the actual optical paths of light rays do not satisfy these assumptions. The thin phase plate approximation leads to about 10% under correction. Accordingly, embodiments of the present invention provide a modified thin phase plate model for calculating the lenticule shape. The modification is based on a comparison between the Munnerlyn model and the thin phase plate model for spherical aberration.

Figures 3, 4:
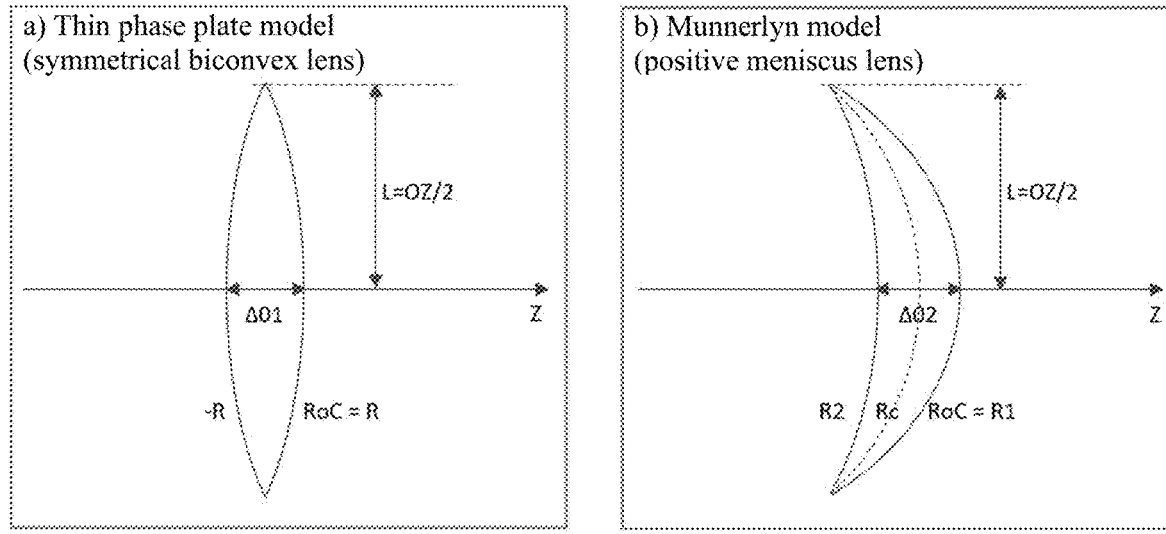
FIG. 3 schematically illustrates a biconvex lenticule used in the thin phase plate model and a meniscus lenticule used in the Munnerlyn model.
FIG. 4 shows a table that summarizes calculated values of the Munnerlyn correction factor applied to the thin phase plate model according to embodiments of the present invention.

The Munnerlyn model (or Munnerlyn formula) is a conventional technology used to calculate corneal lenticule shapes based on the amount of desired correction of the manifest refractive power. The Munnerlyn model is applied to a cornea in a free eye, so the lenticule has the shape of a positive meniscus lens. (Note that the descriptions here use correction for myopic error as an example.) FIG. 3 schematically illustrates the relation between lenticule thickness for a symmetrical biconvex lenticule used in the thin phase plate model and a meniscus lenticule used in the Munnerlyn model.

The biconvex lenticule in the thin phase plate model is formed by two lenticule surfaces having radius of curvature (RoC) R and −R, respectively. The center thickness of the lenticule is denoted $\Delta_{01}$. The meniscus lenticule in the Munnerlyn model is formed by two lenticule surfaces having radius of curvature $R_1$ and $R_2$, respectively. The center thickness of the lenticule is denoted $\Delta_{02}$. For both lenticules, the optical zone (i.e., the part of the lenticule that effectuates optical correction) has a diameter OZ and radius L=OZ/2.

The optical power P of the biconvex lenticule in the thin phase plate model is:

$$P = \frac{1}{f} = (n_c - 1) \cdot \left(\frac{1}{R} - \frac{1}{(-R)}\right) = \frac{2(n_c - 1)}{R}$$

where f is the focal length of the lenticule. Using $$R \cong \frac{L^2}{\Delta_{01}}$$

one obtains (Eq. (2)):

$$\frac{\Delta_{01}}{P} = \frac{L^2}{2(n_c - 1)}$$

This result may also be derived from the thin phase plate model wavefront calculation.

The optical power P of the positive meniscus lenticule in the Munnerlyn model is:

$$P = \frac{1}{f} = (n_c - 1) \cdot \left(\frac{1}{R_1} - \frac{1}{R_2}\right)$$

$R_1$ and $R_2$ may be expressed by an average radius of curvature $R_c$ and a parameter $\alpha$ as:

$$R_1 = R_c - \alpha \cdot \Delta_{02}, R_2 = R_c + \alpha \cdot \Delta_{02}$$

which gives (Eq. (3)):

$$\frac{\Delta_{01}}{P} = \frac{R_c^2}{2(n_c - 1) \cdot \alpha}$$

It can be shown that $$\Delta_{02} = \frac{H(R_1, L) - H(R_2, L)}{1 - \frac{(n_C - 1)}{n_C} \cdot H'(R_2, L)} = \frac{H(R_c, L)(-2\alpha \cdot \Delta_{02})}{1 - \frac{(n_C - 1)}{n_C} \cdot H'(R_c, L)}$$

where H is the sagitta function, i.e., the cord height of a circular arc, $H(R, L) = R - \sqrt{R^2 - L^2}$, where R is R1, R2, or Rc; H' is the partial derivative of H with respect to R, $$H'(R, L) = \frac{\partial H}{\partial R} = 1 - R/\sqrt{R^2 - L^2}.$$

Therefore:

$$\frac{1}{\alpha} = \frac{-2H'(R_c, L)}{1 - \frac{(n_C - 1)}{n_C} \cdot H'(R_c, L)}$$

and Eq. (3) becomes:

$$\frac{\Delta_{02}}{P} = \frac{R_c^2}{2(n_c - 1)} \cdot \frac{-2H'(R_c, L)}{1 - \frac{(n_c - 1)}{n_c} \cdot H'(R_c, L)} =$$

$$\frac{L^2}{2(n_c - 1)} \cdot \frac{2R_c^2}{\left[\frac{n_c - 1}{n_c} \cdot L^2 + \sqrt{R_c^2 - L^2} \cdot \left(R_c + \sqrt{R_c^2 - L^2}\right)\right]}$$

Therefore, the ratio of $\Delta_{02}$ of the meniscus lenticule in the Munnerlyn model to $\Delta_{01}$ of the biconvex lenticule in the thin phase plate model is:

$$\frac{\Delta_{02}}{\Delta_{01}} = \frac{2R_c^2}{\left[\frac{n_c - 1}{n_c} \cdot L^2 + \sqrt{R_c^2 - L^2} \cdot \left(R_c + \sqrt{R_c^2 - L^2}\right)\right]}$$

Further, the radius of curvature $R_c$ for any meridian $\varphi$ may be approximated by the average radius of curvature $R_K$, where $$R_K = \frac{R_{K1} + R_{K2}}{2} = \frac{(n_k - 1) \cdot (K_1 + K_2)}{2K_1 \cdot K_2}$$

where $K_1$ and $K_2$ are the flat curvature and steep curvature of the cornea, respectively, and $n_k$ is the refractive index for keratometry (conventionally set at $n_k = 1.3375$).

According to embodiments of the present invention, the factor $\Delta_{02}/\Delta_{01}$, denoted the Munnerlyn correction factor $\gamma_{MT}$, is multiplied to the thickness function calculated by the thin phase plate model (Eq. (1)) to give the corrected thickness function $\Delta(r, \varphi)$ (Eq. (4)):

$$\Delta(r, \varphi) = \frac{2R_K^2}{\left[\frac{n_c - 1}{n_c} \cdot L^2 + \sqrt{R_K^2 - L^2} \cdot \left(R_K + \sqrt{R_K^2 - L^2}\right)\right]} \cdot \frac{W_{max} - W(r, \varphi)}{n_c - 1} \equiv$$

$$\gamma_{MT} \cdot \frac{W_{max} - W(r, \varphi)}{n_c - 1}$$

After applying the Munnerlyn correction factor $\gamma_{MT}$, the lenticule thickness function given by the modified thin phase plate model will agree with the lenticule thickness function given by the Munnerlyn formula for spherical optical power. The correction factor also corrects other aberration components contained in the thickness function calculated from measured wavefront by the thin phase plate model. In other words, the modified thin phase plate model gives a corrected result consistent with the conventional Munnerlyn formula for spherical aberration, while providing corresponding corrections for other aberrations in the measured wavefront.

Although the above derivation of the correction factor $\gamma_{MT}$ uses the Munnerlyn model and a meniscus lenticule defined by radii of curvatures $R_1$ and $R_2$, the resulting correction factor is only a function of $n_c$, $R_K$ and L. Note that $n_c$ is a known value and $R_K$ is readily available from the wavefront aberrometer measurements. FIG. 4 shows a table that summarizes calculated values of the Munnerlyn correction factor applied to the thin phase plate model, as well as the values of lenticule center thickness according to the thin phase plate model and the Munnerlyn model, for a variety of K values and optical zone diameters.

Figure 5:
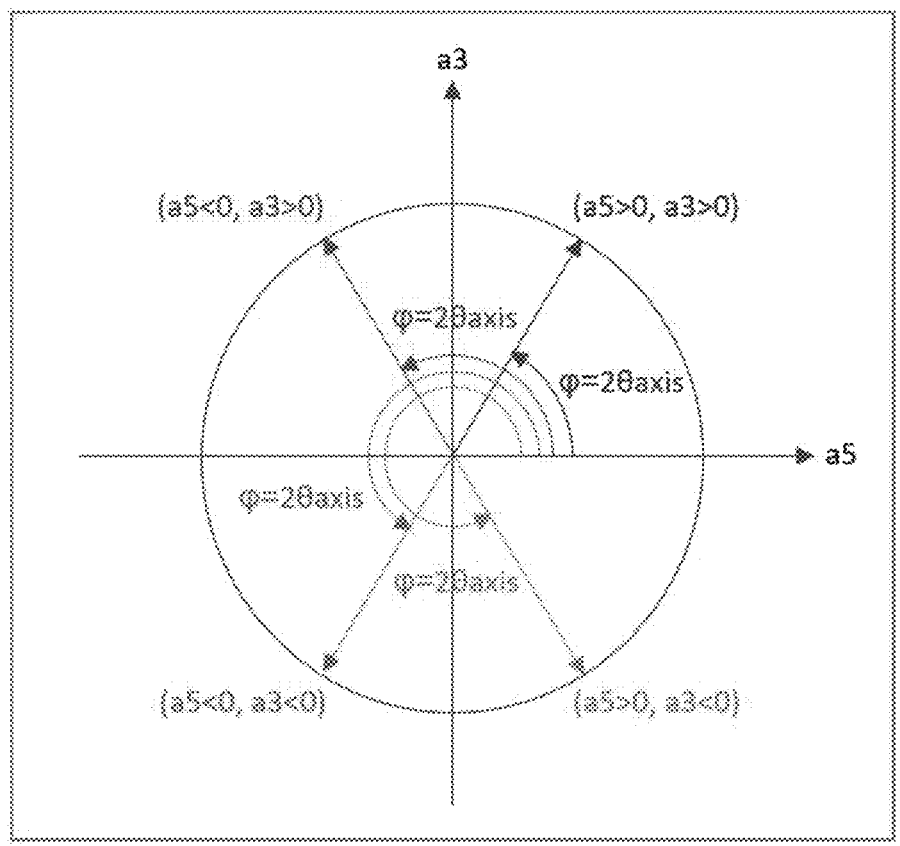
FIG. 5 illustrates the relationship between $\theta_{axis}$ (the axis of the cylindrical power) and signs of the Zernike coefficients.

Relation Between Zernike Coefficients and Manifest Refraction Error, Physician Adjustment The wavefront map contains a spherical power as well as other aberration components. The wavefront map may be represented as a sum of a plurality of Zernike polynomials (a sequence of orthogonal polynomials on a two-dimensional unit disk) with corresponding Zernike coefficients. The relationship between Zernike coefficients and the manifest spherical and cylindrical refraction errors are as follows (Eq. (5)):

$$a_3 \equiv a_{2,-2} = \frac{r_{max}^2 \cdot CYK}{4\sqrt{6}} \cdot \sin(2\theta_{axis})$$

$$a_4 \equiv a_{2,0} = \frac{r_{max}^2}{4\sqrt{3}} \cdot \left(SPH + \frac{CYL}{2}\right)$$

$$a_5 \equiv a_{2,2} = \frac{r_{max}^2 \cdot CYL}{4\sqrt{6}} \cdot \cos(2\theta_{axis})$$

where $a_3 \equiv a_{2,-2}$, $a_4 \equiv a_{2,0}$ and $a_5 \equiv a_{2,2}$ are third, fourth and fifth Zernike coefficients, SPH and CYL are the spherical and cylindrical refractive powers at the cornea plane; and $\theta_{axis}$ is the axis of the cylindrical refractive power. Thus, SPH, CYL, and $\theta_{axis}$ may be calculated from Zernike coefficients $a_3$, $a_4$, and as $a_5$ follows (Eq. (6)):

$$CYL = \pm \frac{4\sqrt{6}}{r_{max}^2} \cdot \sqrt{a_3^2 + a_5^2}$$

$$SPH = -\frac{4\sqrt{6}}{r_{max}^2} \cdot a_4 - \frac{CYL}{2} \text{ and}$$

$$a \equiv SIGN(CYL) \cdot \sqrt{a_3^2 + a_5^2}, \text{ if } a = 0, \theta_{axis} = 0 \quad \text{(Eq. (7))}$$

$$\exp(i \cdot 2\theta_{axis}) = \frac{a_5 + i \cdot a_3}{a}, a \neq 0$$

$$\theta_{axis} = \frac{90°}{\pi} \cdot IMAGINARY\left[IMLN\left(COMPLEX\left(\frac{a_5}{a}, \frac{a_3}{a}\right)\right)\right], a \neq 0$$

$$\theta_{axis} = IF(\theta_{axis} < 0, 180 + \theta_{axis}, \theta_{axis})$$

where it is assumed that the arcsin function returns in radian. The relationship between $\theta_{axis}$ and signs of the Zernike coefficients is illustrated in FIG. 5. This relationship between the lower order Zernike coefficients and the lower order manifest refraction errors (Eqs. (5), (6), (7)) enables verification of the wavefront error with manifest refraction error, and also allows physician adjustment to the low order refraction error, if desired, as described below.

To perform physician adjustment, the relationship between optical powers calculated from the wavefront and manifest optical powers for given measurement conditions should be taken into account. Denote the results calculated in Eq. (6) by $SPH_{wc}$, $CYL_{wc}$, i.e. the spherical and cylindrical refractive power on the cornea plane for optical infinity calculated from wavefront data; denote $SPH_{wm}$, $CYL_{wm}$ the corresponding manifest equivalent under given measurement conditions. It is known that an optical power on the cornea plane for optical infinity, $D_c$, and the manifest equivalent of that optical power, $D_m$, are related to each other by the following equations:

$$D_c = \frac{(L - V) \cdot D_m - 1}{L - V \cdot (L - V) \cdot D_m} \text{ or}$$

$$D_m = \frac{L \cdot D_c + 1}{(L - V) \cdot (1 + V \cdot D_c)}$$

where L is the lane length, i.e. the length of the exam lane, and V is the vertex distance, i.e. the distance between the back surface of a corrective lens and the front of the cornea. Both are parameters describing the manifest refraction measurement conditions. Optical infinity corresponds to L=infinity and cornea plane corresponds to V=0. Applying this relationship to $SPH_{wc}$ and $(SPH_{wc}+CYL_{wc})$ gives (Eq. (8)):

$$SPH_{wm} = \frac{L \cdot SPH_{wc} + 1}{(L-V) \cdot (1 + V \cdot SPH_{wc})}$$

$$P_{wc} \equiv SPH_{wc} + CYL_{wc}, \; P_{wm} \equiv SPH_{wm} + CYL_{wm}$$

$$P_{wm} = \frac{L \cdot P_{wc} + 1}{(L-V) \cdot (1 + V \cdot P_{wc})}$$

$$CYL_{wm} = P_{wm} - SPH_{wm}$$

Figure 6:
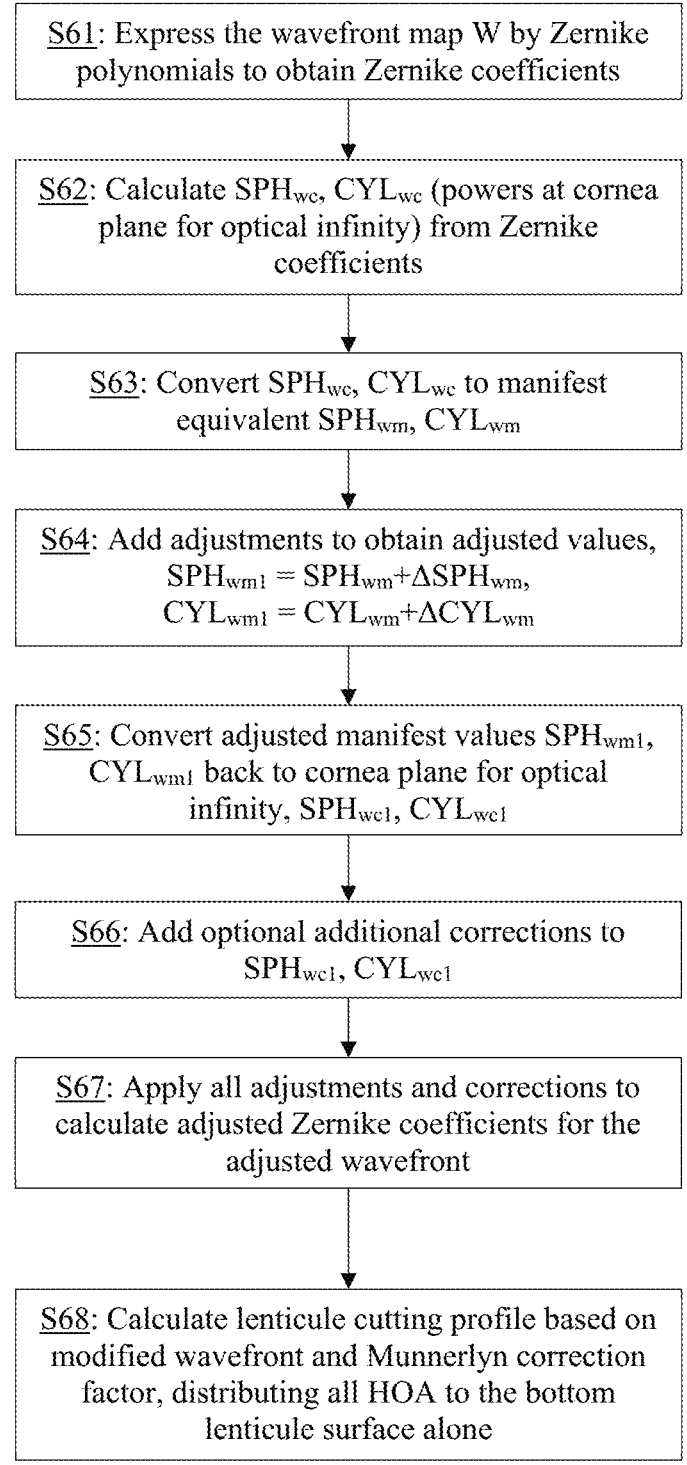
FIG. 6 is a flow diagram illustrating a method of incorporating various adjustments and corrections to calculate the lenticule cutting profile according to embodiments of the present invention.

Using the above relationships, physician adjustment may be calculated as follows (see FIG. 6). After expressing the wavefront map as a sum of Zernike polynomials to obtain the original Zernike coefficients (step S61), the spherical and cylindrical powers at cornea plane for optical infinity, $SPH_{wc}$, $CYL_{wc}$, are calculated from these original Zernike coefficients using Eqs. (6) and (7) (step S62). The powers are converted to equivalent values under manifest measurement conditions L and V, $SPH_{wm}$, $CYL_{wm}$, using Eq. (8) (step S63). Physician adjustments $\Delta SPH_{wm}$, $\Delta CYL_{wm}$ are then added to these equivalent manifest values to obtain adjusted values, $SPH_{wm1}=SPH_{wm}+\Delta SPH_{wm}$, $CYL_{wm1}=CYL_{wm}+\Delta CYL_{wm}$ (step S64). The adjusted values are converted back to cornea plane for optical infinity, $SPH_{wc1}$, $CYL_{wc1}$, using the inverse of Eq. (8) (step S65). This gives adjustments $SPH_{wc1}-SPH_{wc}$, $CYL_{wc1}-CYL_{wc}$ at cornea plane for optical infinity.

Non-Refractive Flat Add

Figure 7:
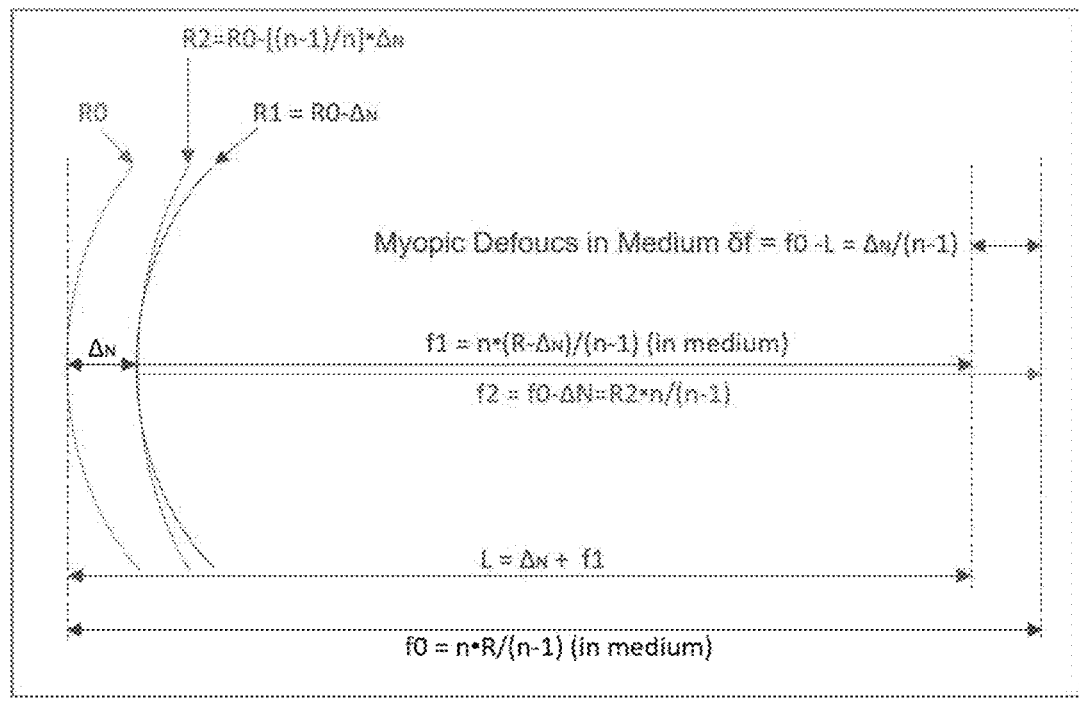
FIG. 7 schematically illustrates a non-refractive flat add that introduces a spherical refractive error.

Other adjustments may be added to the calculated optical powers (step S66), for example, a spherical refractive error introduced by a non-refractive "flat add", described below with reference to FIG. 7.

The non-refractive flat add is a layer of uniform thickness added to the lenticule thickness for purposes of improving the mechanical properties of the lenticule. As shown in FIG. 7, a first surface of a medium having a radius $R_0$ focuses a parallel light to a first focal point in the medium located at the first focal distance $f_0=n^*R_0/(n-1)$ from the apex of the first surface, where n is the refractive index of the medium. A second surface that is concentric with the first surface but have a smaller radius $R_1=R_0-\Delta_N$ focuses a parallel light to a second focal point in the medium located at a second focal distance $f_1=n^*R_1/(n-1)=n^*(R_0-\Delta_N)/(n-1)$ from the apex of the second surface. The second focal point is at a distance $L=\Delta_N+f_1$ from the apex of the first surface. The second focal point does not coincide with the first focal point; it is located before the first focal point by a distance (myopic defocus) $\delta f=f_0-L=\Delta_N^*(n-1)$. In order for a surface (the third surface) that has the same apex as the second surface to focus light at the first focal point, i.e. for the third surface to have a focal distance $f_2=f_0-\Delta_N$, using $f_2=n^*R_2/(n-1)$, the third surface should have a radius $R_2=R_0-((n-1)/n)^*\Delta_N$.

Thus, the flat add (the layer between the first surface and the second surface, with thickness $\Delta_N$) introduces a myopia error given by:

$$\Delta SPH_N = (n_c - 1) \cdot \left(\frac{1}{R_2} - \frac{1}{R_1}\right) = -\frac{(n_c-1)}{n_c} \cdot \frac{\Delta_N}{R_0^2}$$

Here, the first surface ($R_0$) is the cornea anterior surface because only this surface, not the cutting surfaces of the lenticule, has the refractive power. In preferred embodiments, $R_0=R_K$ is used.

This correction is to be added to the spherical power at cornea plane for optical infinity.

Cutting Profile in Cornea Under Applanation

Figure 8:
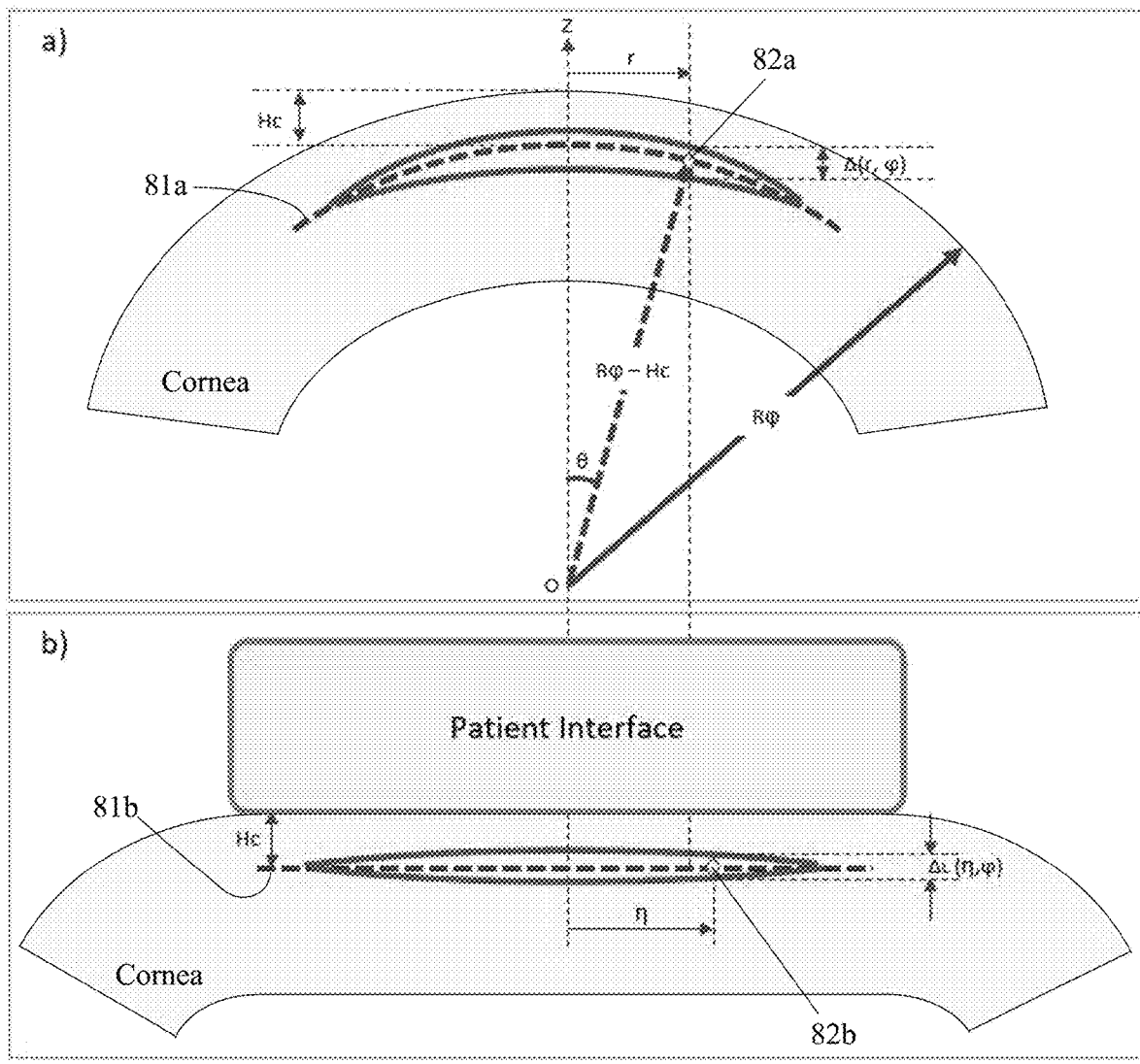
FIG. 8 schematically illustrates the relationship between a lenticule in a free (un-applanated) cornea and an applanated cornea.

To calculate the lenticule profile from the wavefront map, an applanation correction is also required. FIG. 8 schematically illustrates the relationship between a lenticule in a free cornea and an applanated cornea and definitions of parameters for applanation correction. As shown in FIG. 8 (side cross-sectional views, cut along a meridian angle φ around the Z axis), a bi-convex lenticule in the applanated cornea (panel b) corresponds to a meniscus lenticule in the free cornea (panel a). An imaginary straight center line 81b in the applanated cornea, which is parallel to the applanated cornea surface at a distance $H_C$ and passes through the edge of the lenticule, corresponds to an arc 81a in the free cornea having a radius of curvature $R_\varphi-H_C$, where $R_\varphi$ is the radius of curvature of the free cornea at the meridian angle φ. A given point 82b in the applanated cornea located on the center line 81b at a distance η (polar radius after applanation) from the Z axis corresponds to a point 82a in the free cornea located on the arc 81a at a distance r (polar radius before applanation) from the Z axis with a corresponding zenith angle θ. The arc length of the point 82a along the arc 81a is equal to the distance η of the point 82b along the straight line 81b, both measured from the intersections with the Z axis. The thickness of the lenticule in the applanated cornea at the point 82b is denoted $\Delta_L(\eta,\varphi)$, and the thickness of the lenticule in the free cornea at the corresponding point 82a is denoted $\Delta(r,\varphi)$. The relationships among the various parameters are:

$$P(\varphi) = K_1 \cdot \sin^2(\varphi - \Phi_{K2} - \Delta\Phi_c) + K_2 \cdot \cos^2(\varphi - \Phi_{K2} - \Delta\Phi_c)$$

$$R_\varphi = \frac{n_k - 1}{P(\varphi)}$$

$$\theta = \arcsin\left(\frac{r}{R_\varphi - H_C}\right) \text{ for } |r| \le r_{max}$$

$$\eta = (R_\varphi - H_C) \cdot \theta$$

$$\eta_L = (R_\varphi - H_C) \cdot \arcsin\left(\frac{r_{max}}{R_\varphi - H_C}\right)$$

$$\theta = \frac{\eta}{R_\varphi - H_C} \text{ for } |\eta| \le \eta_L$$

$$r = (R_\varphi - H_C) \cdot \sin\theta$$

$$\Delta L(\eta, \varphi) = \Delta(r, \varphi) \cdot \frac{\sin(2\theta)}{2\theta}$$

where $\Phi_{K2}$ is the K2 axis, $\Delta\Phi_c$ is the cyclotorsion rotation angle, $r_{max}$ is the radius of the lenticule in the free cornea, and $\eta_L$ is the radius of the lenticule in the applanated cornea.

The adjustments and corrections can now be applied to calculate adjusted Zernike coefficients for the adjusted wavefront (step S67), and then the lenticule cutting profile (step S68), in the applanated cornea.

Applying all adjustments and corrections to the original Zernike coefficients, the adjusted Zernike coefficients $b_i$ are:

$$b_3 = (1 - \gamma_{LOA}) \cdot \left[a_3 + \frac{r_{max}^2 \cdot \Delta CYL_W}{4\sqrt{6}} \cdot \sin(2\theta_{axis})\right]$$

$$b_4 = (1 - \gamma_{LOA}) \cdot \left[a_4 - \frac{r_{max}^2}{4\sqrt{3}} \cdot \left(\Delta SPH_W + \Delta SPH_N + \frac{\Delta CYL_W}{2}\right)\right]$$

-continued $$b_5 = (1 + \gamma_{LOA}) \cdot \left[ a_5 + \frac{r_{max}^2 \cdot \Delta CYL_w}{4\sqrt{6}} \cdot \cos(2\theta_{axis}) \right]$$

$$b_i = \gamma_{HOA} \cdot a_i \text{ for } i \geq 6 \text{ and } i \neq 12,$$

$$b_{12} = \gamma_{HOA} \cdot a_{12} - C_{SA}$$

where $\Delta SPH_w = SPH_{wc1} - SPH_{wc}$, and $\Delta CYL_w = CYL_{wc1} - CYL_{wc}$; and $\gamma_{LOA}$ (low order lenticule thickness nomogram), $\gamma_{HOA}$ (high order lenticule thickness nomogram) and $C_{SA}$ (for correcting spherical aberration) are physician's adjustment parameters which are input by the physician based on their nomogram (experience).

The first three Zernike polynomials (i=3, 4, 5) are referred to as lower-order aberrations (LOA) and the rest (i≥6; for example, i=6, 7, . . . 14) are referred to as higher-order aberrations (HOA). The adjusted wavefront $W(\rho, \varphi_m)$, expressed as a sum of Zernike polynomials with adjusted Zernike coefficients $b_i$, may be divided into a lower-order part $W_L(\rho, \varphi_m)$ and a higher-order part $W_H(\rho, \varphi_m)$, as follows (where $\rho = r/r_{max}$ which varies between 0 and 1):

$$\varphi_w = \varphi_m - \Theta_{CYC}$$

$$W(\rho, \varphi_m) = \sum_{i=3}^{14} b_i \cdot Z_i(\rho, \varphi_w)$$

$$W_{max} = \max\{W(\rho, \varphi_w)\}$$

$$W_L(\rho, \varphi_m) = \sum_{i=3}^{5} b_i \cdot Z_i(\rho, \varphi_w)$$

$$W_H(\rho, \varphi_m) = \sum_{i=6}^{14} b_i \cdot Z_i(\rho, \varphi_w)$$

The lenticule thickness profile in the applanated cornea can now be calculated from the adjusted wavefront $W(\rho, \varphi_m)$ by applying the Munnerlyn correction factor, using Eq. (4). The shapes of the bottom and top lenticule surfaces (lenticule cutting profile, measured as a depth from the center line) in the applanated cornea, $\Delta_{BOT}$ and $\Delta_{TOP}$, are then calculated from the lenticule thickness profile. It is possible to distribute the lenticule thickness evenly between the bottom and top lenticule surfaces. In embodiments of the present invention, however, the higher-order part is distributed to the bottom lenticule surface alone, while the lower-order part is distributed to both the bottom and top lenticule surfaces:

$$\Delta_{BOT}(\eta, \varphi_m) =$$
$$\frac{\Delta_N}{2} + \frac{\sin(2\theta)}{2\theta} \cdot \gamma_{MT} \cdot \frac{(1 - \gamma_{TOP}) \cdot [W_{max} - W_L(\rho, \varphi_m)] - W_H(\rho, \varphi_m)}{(n_c - 1)}$$

$$\Delta_{TOP}(\eta, \varphi_m) = -\frac{\Delta_N}{2} - \frac{\sin(2\theta)}{2\theta} \cdot \gamma_{MT} \cdot \frac{\gamma_{TOP} \cdot [W_{max} - W_L(\rho, \varphi_m)]}{(n_c - 1)}$$

where $\gamma_{TOP}$ represents the top-to-total ratio of the amount of the lower-order part that is distributed to the top lenticule surface (the rest, $1-\gamma_{TOP}$, is distributed to the bottom lenticule surface). In other words, the bottom lenticule surface contains both HOA part and LOA part, and the top lenticule surface contains only LOA part.

One advantage of distributing the HOA to the bottom lenticule surface alone is that the bottom lenticule incision is typically formed first, where no or negligible gas bubbles have formed in the cornea from photodisruption by the laser beam. Gas bubbles tend to interfere with subsequent cutting, for example, the cutting of the top lenticule surface. Therefore, the shape of the formed bottom surface is generally more accurate than that of the top surface, and can better express the HOA part which typically has smaller magnitude and higher frequency.

In preferred embodiments, each of the bottom and top surfaces has a peripheral transition zone, the shape of which deviate from the above-calculated shapes for the bottom and top surfaces. The center areas of the bottom and top surfaces that have the above-calculated shapes are referred to as the optical zone. The transition zones are employed to improve the mechanical properties of the lenticule and for other beneficial reasons. In preferred embodiments, the lenticule incisions may further include a ring cut that extends near the edge of the lenticule and intersects both the bottom and top surfaces and a pocket cut located outside of the optical zone. Any suitable shapes for the transition zone, ring cut, and pocket cut may be used. An entry cut is also formed to connect the lenticule to the anterior cornea surface for purposes of lenticule extraction.

Figure 9:
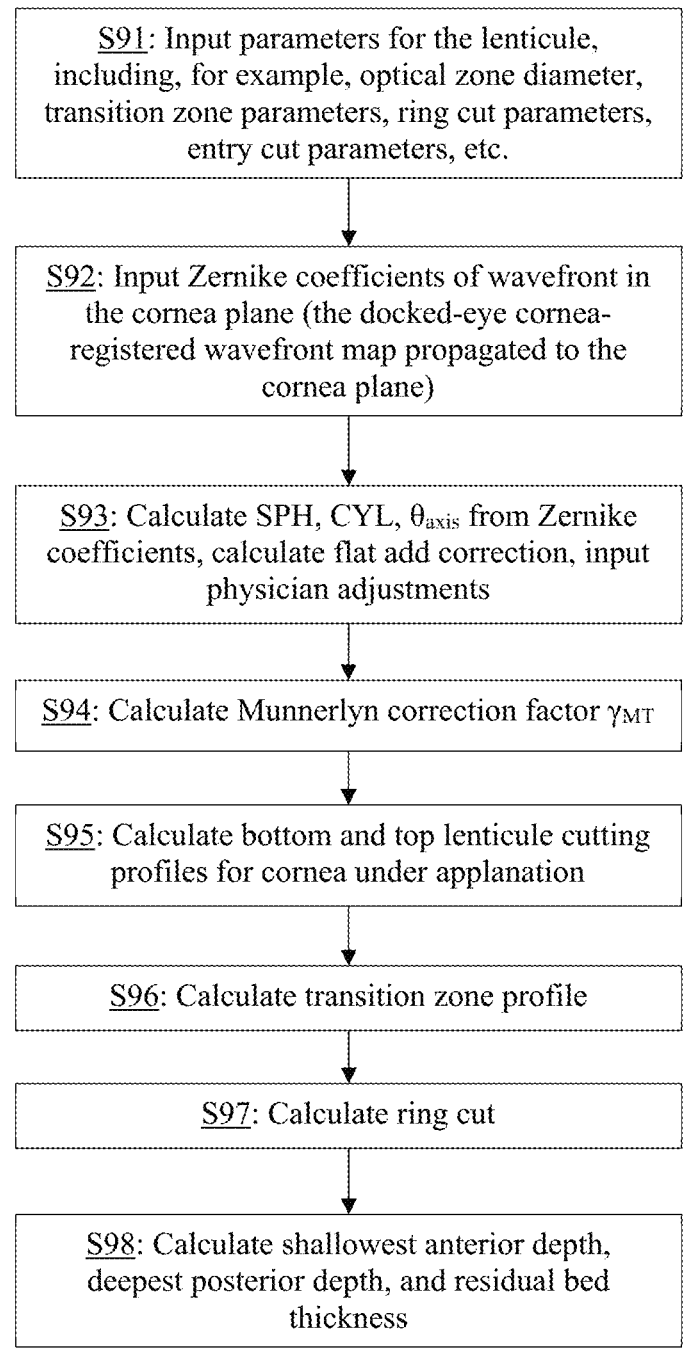
FIG. 9 is another flow diagram illustrating the steps of wavefront-guided corneal lenticule extraction calculation according to embodiments of the present invention.

To summarize, the steps of the wavefront-guided corneal lenticule extraction calculation include the following (FIG. 9):

Step S91: Input parameters for the lenticule, including, for example, optical zone diameter, transition zone parameters, ring cut parameters, entry cut parameters, etc.

Step S92: Calculate Zernike coefficients of the input wavefront (using the docked-eye cornea-registered wavefront propagated to the cornea plane as the input wavefront).

Step S93: Calculate SPH, CYL, $\theta_{axis}$ from Zernike Coefficients; calculate Flat Add correction; calculate physician adjustments.

Step S94: Calculate Munnerlyn correction factor $\gamma_{MT}$.

Step S95: Calculate bottom and top lenticule cutting profiles for applanated cornea, by applying all adjustments and corrections and the Munnerlyn correction factor.

Step S96: Calculate transition zone profile.

Step S97: Calculate ring cut.

Step S98: Calculate shallowest anterior depth, deepest posterior depth, and residual bed thickness.

The Ophthalmic Laser Surgical System

An ophthalmic laser surgical system which may be used to implement embodiments of the present invention is described with reference to FIGS. 10-12.

Figure 10:
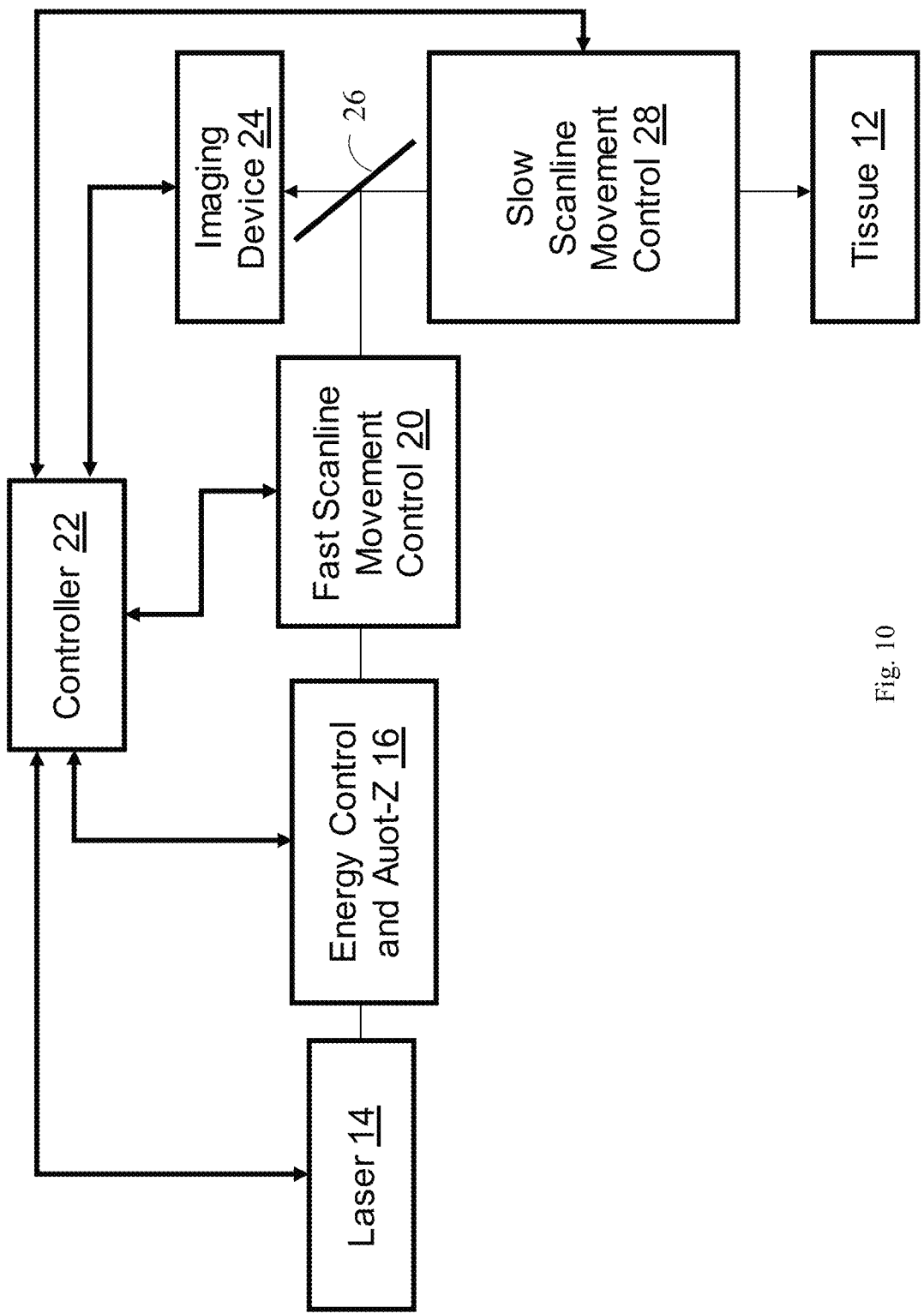
FIGS. 10 and 11 schematically illustrate a surgical ophthalmic laser system which may be used to perform a lenticule incision method according to an embodiment of the present invention.

FIG. 10 shows an ophthalmic laser surgical system 10 for making an incision in a tissue 12 of a patient's eye. The system 10 includes, but is not limited to, a laser 14 capable of generating a pulsed laser beam, an energy control module 16 for varying the pulse energy of the pulsed laser beam, a fast scanline movement control module 20 for generating a fast scanline of the pulsed laser beam (described in more detail later), a controller 22, and a slow scanline movement control module 28 for moving the laser scanline and delivering it to the tissue 12. The controller 22, such as a processor operating suitable control software, is operatively coupled with the fast scanline movement control module 20, the slow scanline movement control module 28, and the energy control module 16 to direct the scanline of the pulsed laser beam along a scan pattern on or in the tissue 12. In this embodiment, the system 10 further includes a beam splitter 26 and a imaging device 24 coupled to the controller 22 for a feedback control mechanism (not shown) of the pulsed laser beam. Other feedback methods may also be used. In an embodiment, the pattern of pulses may be summarized in machine readable data of tangible storage media in the form of a treatment table. The treatment table may be adjusted according to feedback input into the controller 22 from an automated image analysis system in response to feedback data provided from a monitoring system feedback system (not shown).

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the tissue or other material to produce high-precision material processing. For example, a micro-optics scanning system may be used to scan the pulsed laser beam to produce an incision in the material, create a flap of the material, create a pocket within the material, form removable structures of the material, and the like. The term "scan" or "scanning" refers to the movement of the focal point of the pulsed laser beam along a desired path or in a desired pattern.

In other embodiments, the laser 14 may comprise a laser source configured to deliver an ultraviolet laser beam comprising a plurality of ultraviolet laser pulses capable of photodecomposing one or more intraocular targets within the eye.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam toward an eye (for example, onto or into a cornea) for plasma mediated (for example, non-UV) photoablation of superficial tissue, or into the stroma of the cornea for intrastromal photodisruption of tissue. In these embodiments, the surgical laser system 10 may also include a lens to change the shape (for example, flatten or curve) of the cornea prior to scanning the pulsed laser beam toward the eye.

Figure 11:
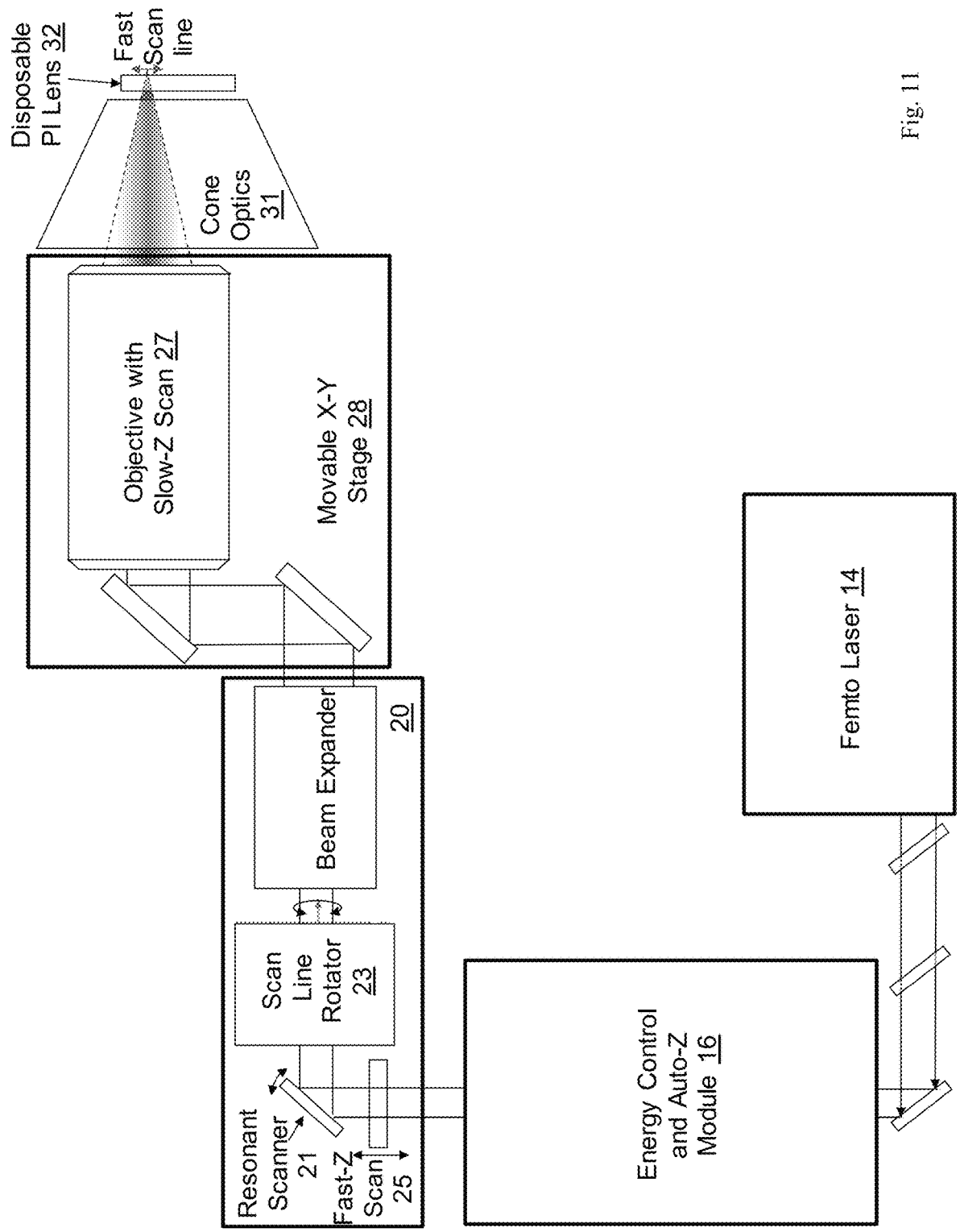

FIG. 11 shows another exemplary diagram of the laser system 10. FIG. 11 shows components of a laser delivery system including a moveable XY-scanner (or movable XY-stage) 28 of a miniaturized femtosecond laser system. In this embodiment, the system 10 uses a femtosecond oscillator, or a fiber oscillator-based low energy laser. This allows the laser to be made much smaller. The laser-tissue interaction is in the low-density-plasma mode. An exemplary set of laser parameters for such lasers include pulse energy in the 40-100 nJ range and pulse repetitive rates (or "rep rates") in the 2-40 MHz range. A fast-Z scanner 25 and a resonant scanner 21 direct the laser beam to a scanline rotator 23. When used in an ophthalmic procedure, the system 10 also includes a patient interface design that has a fixed cone nose 31 and a contact lens 32 that engages with the patient's eye. A beam splitter may be placed inside the cone 31 of the patient interface to allow the whole eye to be imaged via visualization optics. In some embodiments, the system 10 may use: optics with a 0.6 numerical aperture (NA) which would produce 1.1 μm Full Width at Half Maximum (FWHM) focus spot size; and a resonant scanner 21 that produces 0.2-1.2 mm scan line with the XY-scanner scanning the resonant scan line to a 1.0 mm field. The prism 23 (e.g., a Dove or Pechan prism, or the like) rotates the resonant scan line in any direction on the XY plane. The fast-Z scanner 25 sets the incision depth. The slow scanline movement control module employs a movable XY-stage 28 carrying an objective lens with Z-scanning capability 27, referred to as slow-Z scanner because it is slower than the fast-Z scanner 25. The movable XY-stage 28 moves the objective lens to achieve scanning of the laser scanline in the X and Y directions. The objective lens changes the depth of the laser scanline in the tissue. The energy control and auto-Z module 16 may include appropriate components to control the laser pulse energy, including attenuators, etc. It may also include an auto-Z module which employs a confocal or non-confocal imaging system to provide a depth reference. The miniaturized femtosecond laser system 10 may be a desktop system so that the patient sits upright while being under treatment. This eliminates the need of certain opto-mechanical arm mechanism(s), and greatly reduces the complexity, size, and weight of the laser system. Alternatively, the miniaturized laser system may be designed as a conventional femtosecond laser system, where the patient is treated while lying down.

Figure 12:
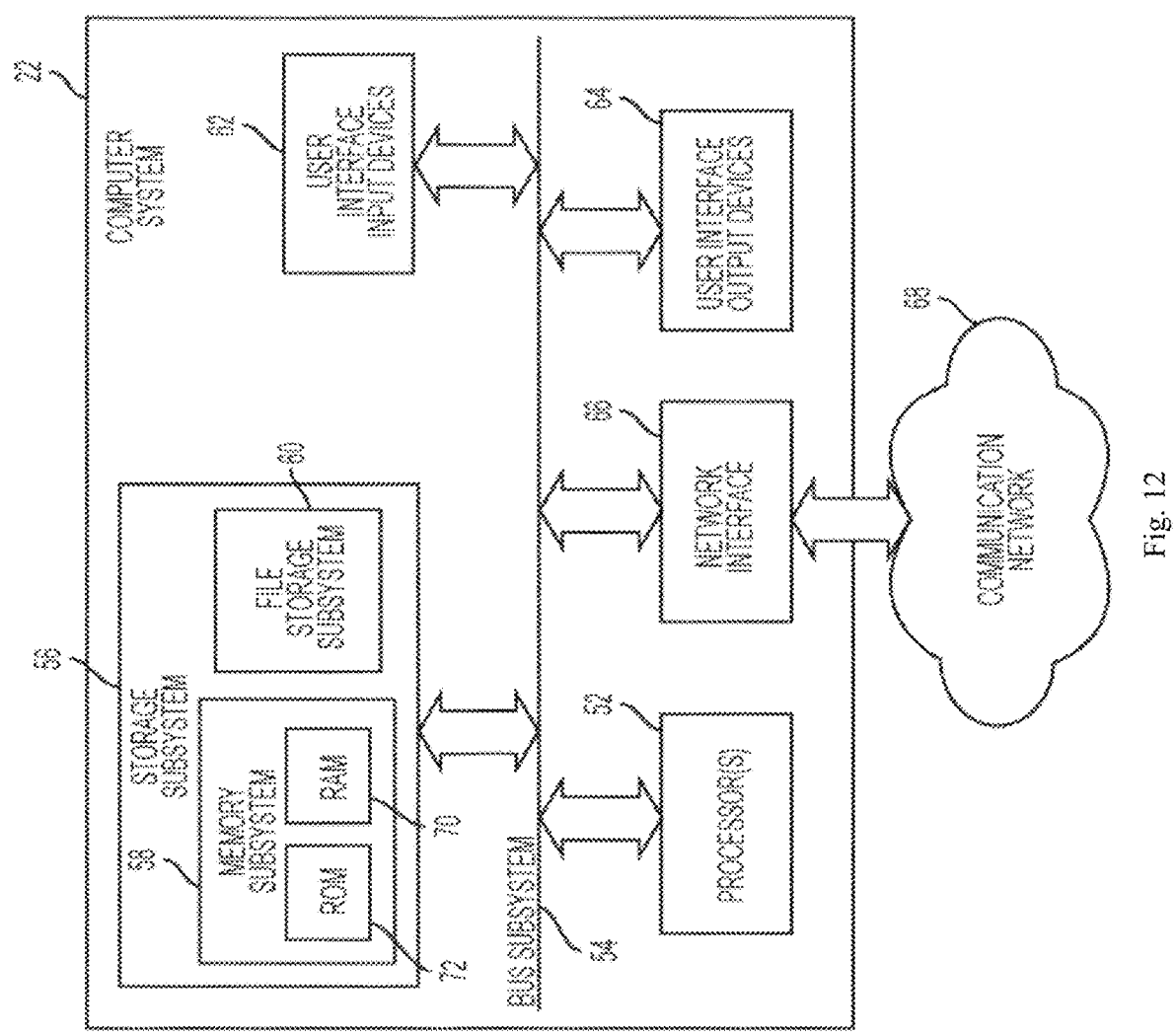
FIG. 12 is a simplified diagram of a controller of a surgical ophthalmic laser system which may be used to perform a lenticule incision method according to an embodiment of the present invention.

FIG. 12 illustrates a simplified block diagram of an exemplary controller 22 that may be used by the laser system 10 according to an embodiment of this invention to control the laser system 10 and execute at least some of the steps discussed in detail below. Controller 22 typically includes at least one processor 52 which may communicate with a number of peripheral devices via a bus subsystem 54. These peripheral devices may include a storage subsystem 56, comprising a memory subsystem 58 (e.g., random access memory (RAM) 70, read only memory (ROM) 72, etc.) and a file storage subsystem 60 (e.g., hard disk drive, optical disc drive, solid-state memory, etc.), user interface input devices 62 (e.g., keyboard, mouse, trackball, touch pad, scanner, foot pedals, a joystick, microphones, etc.), user interface output devices 64 (e.g., display screen, printer, audio output, etc.), and a network interface subsystem 66 (wired or wireless). Network interface subsystem 66 provides an interface to outside networks 68 and/or other devices. Storage subsystem 56 can store the basic programming and data constructs that provide the functionality of the various embodiments of the present invention. For example, a database and modules implementing the functionality of the methods according to embodiments of the present invention, as described herein, may be stored in storage subsystem 56. These software modules are generally executed by processor 52.

Due to the ever-changing nature of computers and networks, the description of controller 22 depicted in FIG. 12 is intended only as an example for purposes of illustrating only one embodiment of the present invention. Many other configurations of controller 22, having more or fewer components than those depicted in FIG. 12, are possible.

As should be understood by those of skill in the art, additional components and subsystems may be included with laser system 10. For example, spatial and/or temporal integrators may be included to control the distribution of energy within the laser beam. Ablation effluent evacuators/filters, aspirators, and other ancillary components of the surgical laser system are known in the art, and may be included in the system. In addition, an imaging device or system may be used to guide the laser beam.

It will be apparent to those skilled in the art that various modification and variations can be made in the wavefront-guided corneal lenticule extraction method and related apparatus of the present invention without departing from the spirit or scope of the invention. Thus, it is intended that the present invention cover modifications and variations that come within the scope of the appended claims and their equivalents.

What is claimed is:

1. A method implemented in an ophthalmic laser system for forming lenticule incisions in a cornea of an eye, comprising:

coupling the eye to the ophthalmic laser system to applanate the eye;

obtaining a wavefront map which has been registered to the cornea of the applanated eye and defined at an anterior surface of the cornea;

calculating a lenticule thickness profile which represents a thickness of cornea tissue to be removed based on the wavefront map and a correction factor using $$\Delta(r, \varphi) = \frac{2R_K^2}{\left[\frac{n_c - 1}{n_c} \cdot L^2 + \sqrt{R_K^2 - L^2} \cdot \left(R_K + \sqrt{R_K^2 - L^2}\right)\right]} \cdot \frac{W_{max} - W(r, \varphi)}{n_c - 1} \equiv$$

$$\gamma_{MT} \cdot \frac{W_{max} - W(r, \varphi)}{n_c - 1}$$

where $\Delta(r, \varphi)$ is the lenticule thickness as a function of a radius r from a Z axis and a meridian angle $\varphi$ around the Z axis, $R_K$ is an average radius of curvature of the cornea anterior surface before applanation, L is a radius of an optical zone of the lenticule, $n_c$ is a refractive index of the cornea, $W(r, \varphi)$ is the wavefront map, $W_{max}$ is a parameter corresponding to a maximum value of the wavefront, and $\gamma_{MT}$ denotes the correction factor;

calculating cutting profiles for a bottom lenticule incision surface and a top lenticule incision surface based on the lenticule thickness profile; and operating the ophthalmic laser system to incise the cornea according to the cutting profiles to form the bottom and top lenticule incision surfaces.

2. The method of claim 1, wherein the step of obtaining the wavefront map includes:

before coupling the eye to the ophthalmic laser system:

using a wavefront aberrometer, measuring an original wavefront map, and taking a first image of the eye including an iris of the eye;

forming a plurality of marks on the cornea;

using a camera of the ophthalmic laser system, taking a second image of the eye including the corneal marks overlaying the iris; and based on the first and second images of the eye, registering the original wavefront map to the corneal marks in the second image to obtain a free-eye cornea-registered wavefront map; and after coupling the eye to the ophthalmic laser system:

using a camera of the ophthalmic laser system, taking a third image of the eye including the corneal marks that have been deformed by the coupling of the eye to the ophthalmic laser system; and based on the second and third images of the eye, registering the free-eye cornea-registered wavefront map to the corneal marks in the third image to obtain the wavefront map.

3. The method of claim 1, wherein the step of obtaining the wavefront map includes:

obtaining an input wavefront map which has been registered to the cornea of the applanated eye and defined at an anterior surface of the cornea;

expressing the input wavefront map as a sum of a plurality of Zernike polynomials to obtain a plurality of original Zernike coefficients;

calculating spherical and cylindrical powers at a cornea plane for optical infinity based on some of the original Zernike coefficients;

converting the spherical and cylindrical powers at the cornea plane for optical infinity to equivalent values of spherical and cylindrical powers under defined manifest measurement conditions;

receiving adjustments of spherical and cylindrical powers as input;

adding the adjustments of spherical and cylindrical powers to the equivalent values of spherical and cylindrical powers to obtain adjusted spherical and cylindrical powers under the defined manifest measurement conditions;

converting the adjusted spherical and cylindrical powers to equivalent values of adjusted spherical and cylindrical powers at the cornea plane for optical infinity;

calculating adjusted Zernike coefficients based on the original Zernike coefficients and the adjusted spherical and cylindrical powers at the cornea plane for optical infinity; and calculating an adjusted wavefront map as a sum of the plurality of Zernike polynomials using the adjusted Zernike coefficients.

4. The method of claim 1, wherein the lenticule thickness profile includes a flat-add layer of uniform thickness, and wherein the step of obtaining the wavefront map includes:

obtaining an input wavefront map which has been registered to the cornea of the applanated eye and defined at an anterior surface of the cornea;

expressing the input wavefront map as a sum of a plurality of Zernike polynomials to obtain a plurality of original Zernike coefficients;

calculating a spherical power at a cornea plane for optical infinity based on some of the original Zernike coefficients;

adding a flat-add correction to the spherical power at the cornea plane for optical infinity, wherein the flat-add correction is a spherical power correction calculated based on the uniform thickness of the flat-add layer;

calculating adjusted Zernike coefficients based on the original Zernike coefficients and the adjusted spherical power at the cornea plane for optical infinity; and calculating an adjusted wavefront map as a sum of the plurality of Zernike polynomials using the adjusted Zernike coefficients.

5. The method of claim 1, wherein the step of calculating the cutting profiles includes:

expressing the wavefront map as a sum of a plurality of Zernike polynomials including a plurality of lower-order Zernike polynomials and a plurality of higher-order Zernike polynomials;

dividing the wavefront map into a lower-order part containing only the lower-order Zernike polynomials and a higher-order part containing only the higher-order Zernike polynomials;

calculating a bottom lenticule incision profile containing all of the higher-order part and a portion of the lower-order part of the wavefront map; and calculating a top lenticule incision profile containing only a remaining portion the lower-order part of the wavefront map and no portion of the higher-order part of the wavefront map.

6. The method of claim 5, wherein the lower-order Zernike polynomials include a third, a fourth and a fifth Zernike polynomials and the higher-order Zernike polynomials a sixth and higher Zernike polynomials.

7. An ophthalmic surgical laser system comprising:
a laser source configured to generate a pulsed laser beam comprising a plurality of laser pulses;
a laser delivery system configured to deliver the pulsed laser beam to a cornea of an eye coupled to the laser delivery system;
an XY-scanner configured to scan the pulsed laser beam in the cornea;
a Z-scanner configured to modify a depth of a focus of the pulsed laser beam; and
a controller configured to control the laser source, the XY-scanner and the Z-scanner to form lenticule incisions in the cornea, including:
obtaining a wavefront map which has been registered to the cornea of the coupled eye and defined at an anterior surface of the cornea;
calculating a lenticule thickness profile which represents a thickness of cornea tissue to be removed based on the wavefront map and a correction factor using $$\Delta(r, \varphi) = \frac{2R_K^2}{\left[\frac{n_c - 1}{n_c} \cdot L^2 + \sqrt{R_K^2 - L^2} \cdot \left(R_K + \sqrt{R_K^2 - L^2}\right)\right]} \cdot \frac{W_{max} - W(r, \varphi)}{n_c - 1} \equiv$$

$$\gamma_{MT} \cdot \frac{W_{max} - W(r, \varphi)}{n_c - 1}$$

where $\Delta(r, \varphi)$ is the lenticule thickness as a function of a radius r from a Z axis and a meridian angle $\varphi$ around the Z axis, $R_K$ is an average radius of curvature of the cornea anterior surface before applanation, L is a radius of an optical zone of the lenticule, $n_c$ is a refractive index of the cornea, $W(r, \varphi)$ is the wavefront map, $W_{max}$ is a parameter corresponding to a maximum value of the wavefront, and $\gamma_{MT}$ denotes the correction factor;
calculating cutting profiles for a bottom lenticule incision surface and a top lenticule incision surface based on the lenticule thickness profile; and
controlling the laser source, the XY-scanner and the Z-scanner of the ophthalmic laser system to incise the cornea according to the cutting profiles to form the bottom and top lenticule incision surfaces.

8. The ophthalmic surgical laser system of claim 7, wherein the step of obtaining the wavefront map includes:
obtaining an input wavefront map which has been registered to the cornea of the applanated eye and defined at an anterior surface of the cornea;
expressing the input wavefront map as a sum of a plurality of Zernike polynomials to obtain a plurality of original Zernike coefficients;
calculating spherical and cylindrical powers at a cornea plane for optical infinity based on some of the original Zernike coefficients;
converting the spherical and cylindrical powers at the cornea plane for optical infinity to equivalent values of spherical and cylindrical powers under defined manifest measurement conditions;
receiving adjustments of spherical and cylindrical powers as input;
adding the adjustments of spherical and cylindrical powers to the equivalent values of spherical and cylindrical powers to obtain adjusted spherical and cylindrical powers under the defined manifest measurement conditions;
converting the adjusted spherical and cylindrical powers to equivalent values of adjusted spherical and cylindrical powers at the cornea plane for optical infinity;
calculating adjusted Zernike coefficients based on the original Zernike coefficients and the adjusted spherical and cylindrical powers at the cornea plane for optical infinity; and
calculating an adjusted wavefront map as a sum of the plurality of Zernike polynomials using the adjusted Zernike coefficients.

9. The ophthalmic surgical laser system of claim 7, wherein the lenticule thickness profile includes a flat-add layer of uniform thickness, and wherein the step of obtaining the wavefront map includes:
obtaining an input wavefront map which has been registered to the cornea of the applanated eye and defined at an anterior surface of the cornea;
expressing the input wavefront map as a sum of a plurality of Zernike polynomials to obtain a plurality of original Zernike coefficients;
calculating a spherical power at a cornea plane for optical infinity based on some of the original Zernike coefficients;
adding a flat-add correction to the spherical power at the cornea plane for optical infinity, wherein the flat-add correction is a spherical power correction calculated based on the uniform thickness of the flat-add layer;
calculating adjusted Zernike coefficients based on the original Zernike coefficients and the adjusted spherical power at the cornea plane for optical infinity; and
calculating an adjusted wavefront map as a sum of the plurality of Zernike polynomials using the adjusted Zernike coefficients.

10. The ophthalmic surgical laser system of claim 7, wherein the step of calculating the cutting profiles includes:
expressing the wavefront map as a sum of a plurality of Zernike polynomials including a plurality of lower-order Zernike polynomials and a plurality of higher-order Zernike polynomials;
dividing the wavefront map into a lower-order part containing only the lower-order Zernike polynomials and a higher-order part containing only the higher-order Zernike polynomials;
calculating a bottom lenticule incision profile containing all of the higher-order part and a portion of the lower-order part of the wavefront map; and
calculating a top lenticule incision profile containing only a remaining portion the lower-order part of the wavefront map and no portion of the higher-order part of the wavefront map.

11. The ophthalmic surgical laser system of claim 10, wherein the lower-order Zernike polynomials include a third, a fourth and a fifth Zernike polynomials and the higher-order Zernike polynomials a sixth and higher Zernike polynomials.

* * * * *